US00PP27361P3

(12) United States Plant Patent
Korlipara

(10) Patent No.: US PP27,361 P3
(45) Date of Patent: Nov. 8, 2016

(54) ***COREOPSIS* PLANT NAMED 'LIGHTNING BUG'**

(50) Latin Name: ***Coreopsis* hybrid**
Varietal Denomination: Lighting Bug

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 88 days.

(21) Appl. No.: 14/544,789

(22) Filed: Feb. 18, 2015

(65) Prior Publication Data

US 2016/0242349 P1 Aug. 18, 2016

(51) Int. Cl.
*A01H 5/02* (2006.01)

(52) U.S. Cl.
USPC ..... Plt./417

(58) Field of Classification Search
USPC ..... Plt./417
See application file for complete search history.

(56) References Cited

PUBLICATIONS

New Plants and Flowers Another Sneak Peek *Coreopsis* 2014, retrieved on Jul. 7, 2016, retrieved from the Internet at <http://www.newplantsandflowers.com/another-sneak-peek-coreopsis/> 2 pp.*

* cited by examiner

*Primary Examiner* — June Hwu
(74) *Attorney, Agent, or Firm* — Klarquist Sparkman, LLP

(57) ABSTRACT

A new and distinct *Coreopsis* plant named 'Lightning Bug' characterized by daisy-type inflorescences that grow to 4 cm in diameter, inflorescences that are gold and red, hardy to Zone 6, maybe lower, grass green foliage on short stems, flowering for the whole summer, a very compact, mounding habit, and excellent vigor.

1 Drawing Sheet

Botanical denomination: *Coreopsis* hybrid.
Variety designation: 'Lightning Bug'.

BACKGROUND OF THE INVENTION

The present invention relates to a new and distinct *Coreopsis* and given the cultivar name 'Lightning Bug'. *Coreopsis* is in the family Asteraceae. This new cultivar originated from a controlled breeding program to produce hardy compact *Coreopsis*. The new cultivar originated from planned cross of two proprietary unnamed *Coreopsis verticillata* hybrid seedlings. The new cultivar of *Coreopsis* is an herbaceous perennial to be grown for landscape and container use in a sunny site.

Compared to the seed parent the new cultivar has a different flower color.

Compared to *Coreopsis* 'Firefly', U.S. Plant Pat. No. 26,295, the new cultivar has flowers that are gold and red rather than yellow with a small red eye.

Compared to *Coreopsis* 'Cosmic Eye', U.S. Plant Pat. No. 22,601, the new cultivar has ray florets that are a gold and red rather than yellow and deep purple. The new cultivar is more dense and compact, with more stems from the crown, and has smaller inflorescences.

SUMMARY OF THE INVENTION

The following traits have been repeatedly observed and are determined to be the unique characteristics of the new variety. These characteristics in combination distinguish *Coreopsis* 'Lightning Bug' as a new and distinct cultivar:

1. daisy-type inflorescences that grow to 4 cm in diameter,
2. inflorescences that are colored gold and red, 3. hardy to USDA zone 6, maybe lower,
4. grass green foliage on short stems,
5. a very compact, mounding habit,
6. flowering for the whole summer, and
7. excellent vigor.

This new cultivar has been reproduced only by asexual propagation (stem and tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an eight month old *Coreopsis* 'Lightning Bug' growing in a one gallon container in full sun in July in Canby, Oreg.

FIG. 2 shows a group of nine-month-old *Coreopsis* 'Lightning Bug' growing in the ground in full sun in the trial field in late August in Canby, Oreg.

DETAILED PLANT DESCRIPTION

The following is a detailed description of the new *Coreopsis* cultivar based on observations of nine-month-old specimens growing in the trial beds in full sun in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart*, 2007.

Plant:

*Type*.—Herbaceous perennial.

*Hardiness*.—USDA Zones 6 to 9.

*Size*.—37 cm wide and 34 cm tall to top of inflorescences.

*Form*.—Mound.

*Vigor*.—Excellent.

*Roots*.—Fibrous, stems root easily from stem cuttings.

Stem:

*Type*.—Ascending, well branched.

*Size*.—Grows to 17 cm tall to where branches for flowering and 5 mm wide.

*Number of stems from the crown*.—About 20.

*Branching habit*.—Freely branched, an average of 8 lateral branches with secondary branches, branches are opposite in arrangement, new lateral flowering branches are continuously produced throughout the summer.

*Internode length*.—2.5 cm to 3 cm.

*Surface*.—Glabrous.

*Color*.—Green N137A.

Leaf:

*Type*.—Simple.

*Shape*.—Pinnately 3-parted with thread-like segments, to linear on top leaves.

*Arrangement*.—Opposite.

*Size*.—To 8 cm wide and 5.3 cm long, the linear segments can grow to 50 mm long and 3 mm wide.

*Apex*.—Acute.

*Margins*.—Entire.

*Petiole*.—0 mm to 2 mm long and 1 mm wide, Green 137A.

*Surface texture*.—Sparsely pubescent on both sides.

*Venation*.—Pinnate, visible main vein the same color as the leaf on both sides.

*Color*.—Topside Green N137A, bottom side Green N137C.

Inflorescence:

*Type*.—Long stalked terminal heads of daisy type inflorescences.

*Peduncle*.—Grows to 4 cm long, 1 mm wide, glabrous, Green N137A.

*Size*.—Grows to 4.5 cm wide and 10 mm deep.

*Immature* (*i.e. the "Flower bud"*).—Globular, 4.5 mm wide and 6 mm deep, Green 137A, glabrous.

*Receptacle*.—Disc shaped, 2.5 mm wide and 1.2 mm deep, Yellow Green 145B.

*Phyllaries*.—In 2 series; upper series surround florets, campanulate, 9 lobes in number, in an area 5 mm deep and spreading 4 wide mm wide, each lobe ovate, 4 mm to 5 mm long and 2 mm to 2.5 mm wide, margin entire, tip acute, glabrous on both sides, both sides Yellow Green 146B; lower series at base of inflorescence, stellate, 5 to 7 in number, in an area 2 mm deep and spreading 7 mm wide, each lobes linear, 5 mm long and 1 mm wide, margin entire, tip acute, Green N137A.

*Lastingness*.—Each inflorescence lasts about a week on the plant.

Florets:

*Type*.—Composite.

*Ray florets*.—8 in number with no pistil or stamen, grow to 22 mm long, 10 mm wide, obovate, with the tip acute and top irregularly notched, side margins entire, glabrous on both sides; topside Yellow Orange 16B on top ⅓ blending to Greyed Purple 187A on ⅔, bottom side Greyed Yellow 162A on top ⅔ blending to Greyed Orange N167A on bottom ⅓.

*Disc*.—Rounded 9 mm wide and becoming 3 mm deep with maturity, Greyed Purple 187B.

*Disc florets*.—Tubular, with stamen and pistil, about 35 in number, 8 mm long and 1 mm wide, tubular; corolla 4 mm long, 5 lobed, tube Yellow Orange 17C, lobes Greyed Purple 187A; pistil 1, 8 mm long, ovary 3 mm long, Greyed Yellow 161A, style 5 mm long, with extruding, 2-branched stigma, stigma and style Orange 26A; stamen 5, anthers 1.2 mm long, Greyed Brown N199B, pollen none.

*Bloom period*.—June to August and will rebloom if trimmed back in Canby, Oreg.

*Fragrance*.—None.

*Seed*.—None seen.

*Fertility*.—Poor.

Disease and pests: No pests or diseases have been observed on plants grown under commercial conditions in Canby, Oreg. No resistances are known.

I claim:

1. A new and distinct *Coreopsis* plant as herein illustrated and described.

* * * * *

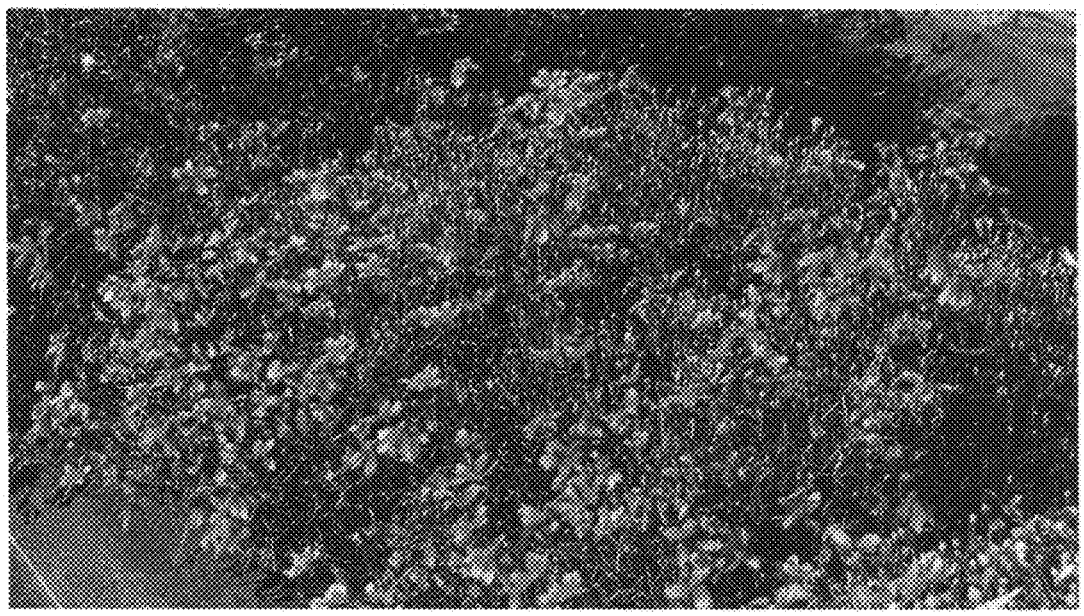

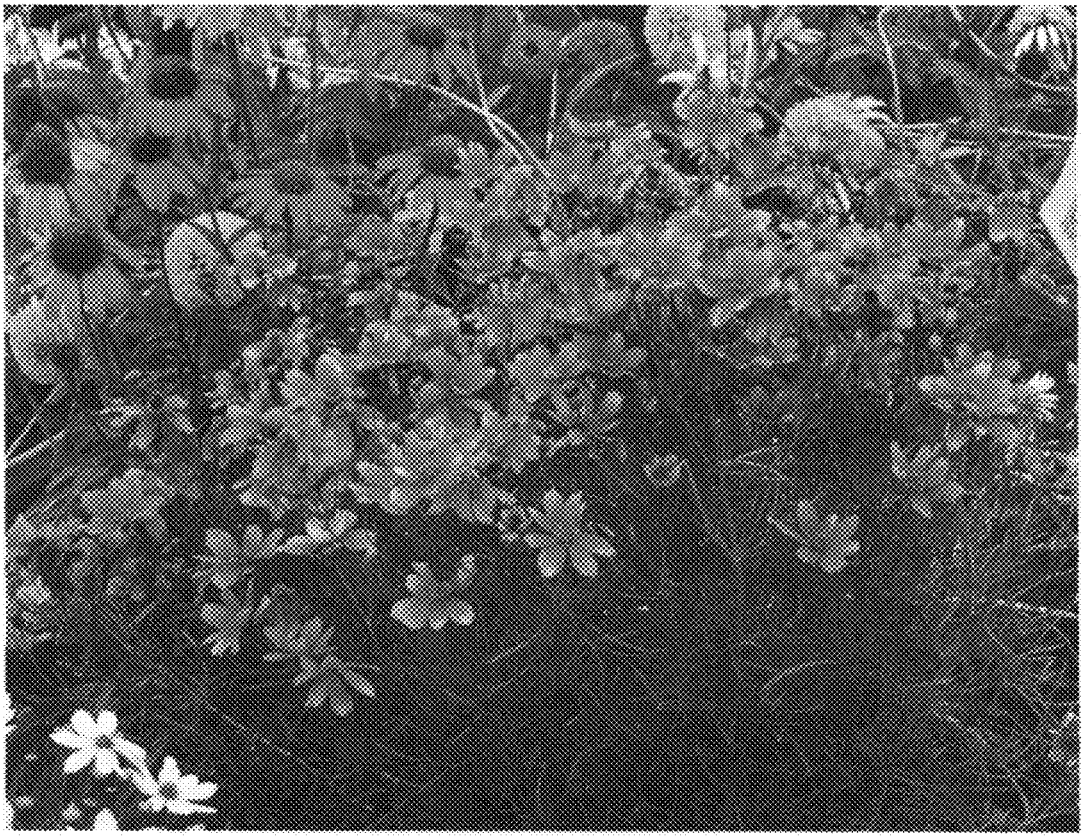
FIG. 1 above, FIG. 2 below